United States Patent
Stepien

(10) Patent No.: US 10,238,300 B2
(45) Date of Patent: Mar. 26, 2019

(54) CONTACT THERMO-OPTICAL STRUCTURE AND ITS APPLICATION FOR NON-INVASIVE IMAGING OF HISTAMINE-INDUCED HYPERTHERMAL SUBCUTANEOUS REACTION MAGNITUDE IN CUTANEOUS ALLERGIC REACTION, RECORDING DEVICE AND METHOD OF ALLERGIC REACTION DIAGNOSIS

(71) Applicant: NEXUS EKSPERTYZY I BADANIA DR JACEK STEPIEN, Warsaw (PL)

(72) Inventor: Jacek Stepien, Warsaw (PL)

(73) Assignee: Nexus Ekspertyzy I Badania Dr Jacek Stepień, Warsaw (PL)

( * ) Notice: Subject to any disclaimer, the term of this patent is extended or adjusted under 35 U.S.C. 154(b) by 452 days.

(21) Appl. No.: 14/901,982

(22) PCT Filed: Dec. 30, 2014

(86) PCT No.: PCT/IB2014/067418
§ 371 (c)(1),
(2) Date: Dec. 29, 2015

(87) PCT Pub. No.: WO2016/108071
PCT Pub. Date: Jul. 7, 2016

(65) Prior Publication Data
US 2016/0367152 A1    Dec. 22, 2016

(51) Int. Cl.
*A61B 5/00*    (2006.01)
*A61B 5/01*    (2006.01)
(Continued)

(52) U.S. Cl.
CPC .............. *A61B 5/015* (2013.01); *A61B 5/411* (2013.01); *A61B 5/445* (2013.01); *A61B 5/6833* (2013.01);
(Continued)

(58) Field of Classification Search
CPC ......... A61B 5/015; A61B 5/411; A61B 5/445; A61B 90/361
See application file for complete search history.

(56) References Cited

U.S. PATENT DOCUMENTS

| 4,302,971 A | 12/1981 | Luk |
| 4,809,707 A * | 3/1989 | Kraft .................... A61B 5/411 |
| | | 600/549 |

(Continued)

FOREIGN PATENT DOCUMENTS

| WO | 2006/086001 A2 | 8/2006 |
| WO | 2008/082318 A1 | 7/2008 |
| WO | 2013/118067 A2 | 8/2013 |

OTHER PUBLICATIONS

ISA/EPO Authorized Officer: Nicola Toto, International Search Report and Written Opinion dated Jul. 14, 2015 in International Application No. PCT/IB2014/067418, total 11 pages.

*Primary Examiner* — Max Hindenburg
(74) *Attorney, Agent, or Firm* — Masuvalley & Partners

(57) ABSTRACT

A passive planar thermo-optical structure for detection of a region of changed temperature on patient's skin is provided. The thermo-optical structure has a layered structure including a transparent film layer, a thermochromic layer, a securing layer, an adhesive layer, and a protective layer. At least one dye in the thermochromic layer is above a temperature threshold range of 31°-37° C., which adopts the first color and keeps it in a temperature range greater than or equal to 0.6° C. A width of this temperature range, in which the color is indefinite, is smaller than 0.3° C.

A method of diagnosing allergy using the above-structure is provided. The method includes the steps of stimulation, measurement and comparison. After stimulating three regions of patient's skin, an evaluation of extent of hista- (Continued)

mine reaction is performed. Then, the extent of histamine reaction in the third region is compared to that in the first and second regions.

6 Claims, 3 Drawing Sheets

(51) Int. Cl.
*G01K 11/16* (2006.01)
*G01K 13/00* (2006.01)
*A61B 90/00* (2016.01)
*A61B 90/30* (2016.01)

(52) U.S. Cl.
CPC .......... *A61B 90/361* (2016.02); *G01K 11/165* (2013.01); *G01K 13/002* (2013.01); *A61B 2090/309* (2016.02); *A61B 2562/0276* (2013.01)

(56) References Cited

U.S. PATENT DOCUMENTS

| | | | |
|---|---|---|---|
| 8,795,675 B2* | 8/2014 | Wang | A61K 39/0003 424/185.1 |
| 9,000,933 B2* | 4/2015 | Ray | G08B 21/043 340/627 |
| 9,011,350 B2* | 4/2015 | Hein, Jr. | A61B 5/445 600/556 |
| 2012/0316458 A1 | 12/2012 | Rahman et al. | |

* cited by examiner

|  | Liquid-crystal mixture I with thermochromic responsiveness in temperature from 32.5°C to 34.3°C | | Liquid-crystal mixture II with thermochromic responsiveness in temperature from 34.3 °C to 36.1°C | |
| --- | --- | --- | --- | --- |
| the colour of light selectively reflected in mesophase | wavelength of light $\lambda_n$(nm) selectively reflected in mesophase | temperature $T_b$(°C) of the beginning of the range of primary colour appearance | wavelength of light $\lambda_n$(nm) selectively reflected in mesophase | temperature $T_b$(°C) of the beginning of the range of primary colour appearance |
| Red | 697.01 | 32.50 | 701.02 | 34.30 |
| Green | 558.12 | 33.10 | 551.11 | 34.90 |
| Blue | 489.03 | 33.70 | 487.07 | 35.50 |

Fig. 3

|  | Liquid-crystal mixture I with thermochromic responsiveness in temperature from 32.5°C to 34.3°C | | Liquid-crystal mixture II with thermochromic responsiveness in temperature from 34.3 °C to 36.1°C | |
| --- | --- | --- | --- | --- |
| the colour of light selectively reflected in mesophase | temperature $T_b$(°C) of the beginning of the range of primary colour appearance | temperature $T_e$(°C) of the end of the range of primary colour appearance | temperature $T_b$(°C) of the beginning of the range of primary colour appearance | temperature $T_e$(°C) of the end of range of primary colour appearance |
| First colour/fourth colour | 32.50 | 33.09 | 34.30 | 34.89 |
| Second colour/fifth colour | 33.10 | 33.69 | 34.90 | 35.49 |
| Third colour/sixth colour | 33.70 | 34.30 | 35.50 | 36.1 |

Fig. 4

| Liquid-crystal mixture I with thermochromic responsiveness in temperature from 32.5°C to 34.3°C | | Liquid-crystal mixture II with thermochromic responsiveness in temperature from 34.3 °C to 36.1°C | |
|---|---|---|---|
| Name of chemical compound | Part by weight [%] | Name of chemical compound | Part by weight [%] |
| cholesteryl nonanoate | 51.38 | cholesteryl nonanoate | 52.53 |
| cholesteryl oleylcarbonate | 47.63 | cholesteryl oleylcarbonate | 46.47 |
| cholesteryl propionate | 0.27 | cholesteryl propionate | 0.18 |
| cholesteryl chloride | 0.14 | cholesteryl chloride | 0.16 |
| cholesteryl benzoate | 0.09 | cholesteryl benzoate | 0.05 |
| 4,4´dipentyl azoxybenzene | 0.49 | 4,4´dipentyl azoxybenzene | 0.61 |

Fig. 5

CONTACT THERMO-OPTICAL STRUCTURE AND ITS APPLICATION FOR NON-INVASIVE IMAGING OF HISTAMINE-INDUCED HYPERTHERMAL SUBCUTANEOUS REACTION MAGNITUDE IN CUTANEOUS ALLERGIC REACTION, RECORDING DEVICE AND METHOD OF ALLERGIC REACTION DIAGNOSIS

RELATED APPLICATIONS

This application is a U.S. National Phase application under 35 U.S.C. § 371 of International Patent Application No. PCT/IB2014/067418 filed Dec. 30, 2014, which is hereby expressly incorporated by reference in its entirety for all purposes.

FIELD OF INVENTION

The invention relates to a contact thermo-optical structure for application on the skin, application of this thermo-optical structure for allergic reaction assessment based on the magnitude of a histamine-induced hyperthermal subcutaneous reaction, a recording device and a method of allergic reaction diagnosis.

BACKGROUND OF THE INVENTION

The allergic reaction of type I, i.e. immediate, as well as in allergic reaction of type IV, i.e. delayed, according to Gell and Coombs classification, in case of skin provocation tests is accompanied by histamine release, i.e. β-Imidazol-ethanamine, what causes a local subcutaneous hyperthermia. This hyperthermia occurs due to activation of H1 receptors located on the surface of the capillary arterioles endothelium, causing their expansion and in consequence an increased blood flow. This increased blood flow provides an endogeneous heat source, revealed subcutaneously as a focal hyperthermia, and on the surface of skin as an erythema, the so-called elevated temperature erythema.

Low values of thermal conductivity coefficient of the skin cause that the effect of heat diffusion via thermal conduction from a point heat source in the location of allergen introduction can be neglected. In consequence, as disclosed in publication by Wong et al., "Minimal role for H1 and H2 histamine receptors in cutaneous thermal hyperemia to local heating in humans", Journ. Appl Physiol., 2006, it can be assumed that the diameter of the elevated temperature area observed on the surface of the skin, i.e. the erythema, corresponds directly to the size of the heat source resulting from increased blood perfusion enforced by the histamine diffusing in the skin. This is an observed specific dermothermal effect resulting only from vasodilatory action of the histamine released during the allergic reaction of skin, wherein the effect is not to be associated with other accompanying patophysiological processes, in particular those induced by inflammatory mediators.

In previous methodology for reading the results of allergy provocation skin tests a subjective quantitative measure in the form of 5 point scale has been applied. In order to determine if an immediate allergic reaction to an introduced allergen has occurred, the diameter of the resulting erythema is measured ca. 15 minutes after performing the test with a ruler scaled in millimeters, as a reaction for the tested substance, next the diameter is compared to the diameter of a reference reaction to introduced histamine with concentration of 1 mg/ml and with a control test with the use of physiological saline (NaCl) solution with concentration of 0.9%.

The extent of the erythema is considered to be a qualitatively-quantitative indicator of positive result of allergy test. However, a direct visual evaluation of the skin test result is not an objective method and has a number of drawbacks coming directly from large variability of the reaction characteristics in short time intervals.

A clinical problem is precise and objective determination, based on the size of the erythema, if the examined patient, i.e. a child, an adult or an elder person.

In fact is allergic to the specific introduced allergen, since only a ruler and the examiner's eye are used for this purpose on standard basis. The scientific literature implies, that the measurable this way allergic reaction having the form of an erythema, resulting from a reaction provoked by the introduction of an allergen causing mast cells degranulation and release of histamine acting vasodilatory, if positively correlated with focally increased skin temperature from 1.5° C. to 2.5° C., wherein the surfaces of allergic reaction registered by thermographic instruments are 3 to 5 times larger than changes visually recognizable on the skin. This means that thermography allows to image the actual extent of the hyperthermia occurring subcutaneously during allergic reaction, in contrast to epidermic erythema being only a visual symptom of this hyperthermia. A thermographic device functions in this case as a converter and a thermo-optical intensifier of thermal image of the histamine reaction, and specifically the vasodilatory component of this reaction, resulting in hyperthermia generated in a cascade of processes in response to the introduced allergen.

The application of thermography enables objective determination of the actual intensity of the skin allergic response measured by the extent of the subcutaneous vascular hyperthermia, producing a colour image of temperature distribution around the allergen introduction location and on the surface of the surrounding skin and allowing for a precise measurement of the diameter of the actual hyperthermal reaction, and not its external symptom having the form of an erythema, promoting correct diagnosis. The usefulness of thermography, this time remote, by means of an infrared camera comprising a cooled bolometer and connected to a computer, recording emission of heat from the surface of the examined skin, for measuring the allergic response has been already pointed out by Bagnato et al. "Measurement of allergen-induced skin reactions by computerized dynamic telethermography", Journ. Investig Allergol Clin Immunol., 1997. In the experiment described therein the patients have been subjected to point skin tests with the use of a set of allergens, a neutral control solution, e.g. 0.9% NaCl, as well as histamine solutions.

In the European patent application EP0189381 there is disclosed a system for acquiring thermographic images of body surface by means of a camera directed towards a liquid-crystal plate, wherein the detector system comprises a non-thermally calibrated liquid-crystal plate, therefore the transformation of the recorded image occurred due to the operation of software, what makes it impossible to precisely filter out the epidermic hyperthermia, what is necessary in dermatological diagnostics.

The solutions known in the state of the art are not suitable for application for the purposes of clinical dermatological diagnostics because of significant complication of operations to be undertaken during calibration, and also because of susceptibility to changes of thermal background temperature of the examined region of skin, what makes it impossible to precisely separate the images of the actual allergic hyperthermia from artefacts arising from the contributed thermal propagation from other epidermic changes related to the patient's health.

The object of the invention is to solve the mentioned problems.

SUMMARY OF THE INVENTION

A passive planar thermo-optical structure for detection of a region with changed temperature on a patient's skin, comprising a thermoactive dye, according to the invention is characterised in that it has a layered structure including a layer of a transparent film, a thermochromic layer, a securing layer, an adhesive layer and a protective layer. At least a portion of the transparent layer's surface forms a screen. At least one dye in the thermochromic layer is characterised in that above a temperature threshold having the value in the range of 31° C. to 37° C. it adopts the first colour and keeps it in the range of temperatures wider than or equal to 0.6° C., and the width of the temperature range, where the colour of the light reflected from the thermo-optical structure is not defined is smaller than 0.3° C. The securing layer prevents mixing of the dye with the adhesive in the adhesive layer. The adhesive layer provides good adhesion of the system being applied on skin and uniform thermal resistance between the skin and the thermo-optical structure throughout its whole surface. The protective layer makes it possible to protect the adhesive layer and isolate it from the environment and contaminants during storage and transport. The protective layer is peeled just before the application of the system on a patient's skin.

The width of the temperature range where the dye keeps the first colour greater than or equal to 0.6° C. provides that local temperature variations will be mapped in the same colour and will not disturb the evaluation of the histamine reaction extent. The width of the transitional range impacts the accuracy of mapping of the temperature changes region extent into the changed colour region. The quicker the transition, the better, but generally values lower than 0.3° C. provide satisfactory results. In result, the combination of values of the transitional temperature range narrower than 0.6° C. with the width of the constant first colour region provides a precise mapping of the histamine reaction, which is accurate and undistorted by the mapping of the natural temperature distribution on the skin surface.

The temperature threshold should fit within the range of 31 to 37 Celsius degrees, in which range fit the vast majority of temperatures observed on skin of patients subjected to allergic tests. Subjecting ill patients to these tests is unfounded. The temperature threshold of the thermosensitive should be selected individually for determined temperature of the patient's skin. According to the invention there is provided a set of these systems, from which set one is selected for a particular patient examination.

The colour of the system for temperatures below the temperature threshold can be transparency. In this case the contrast of colour mapping on the thermo-optical structure's surface can be increased by application of an additional absorber layer. Further improvement of the contrast can be achieved by using for selected colours an additional layer of an optical filter applied on a film layer at the side opposite to the thermochromic layer. The filter's task is to eliminate reflected light within the wavelength range outside of the measurement range. E.g. waves from the range of 589 to 700 nm can be eliminated by the application in the thermochromic layer a blue turning dye, or waves from the range of 400 to 500 nm can be eliminated by the application in the thermochromic layer a red turning dye. Additionally, due to the application of the filter the width of the temperature range, where the colour of the light reflected from the system is not defined, becomes smaller.

Preferably, the thermochromic layer comprises a dye adopting the first colour for temperatures above the temperature threshold within the range of 32.5° C. to 33.1° C.

Preferably, the dye adopts a second colour for temperatures higher than a temperature threshold within the range of 33.1° C. to 33.7° C.

Preferably, the dye adopts a third colour for temperatures higher than a temperature threshold within the range of 33.7° C. to 34.3° C.

Preferably, the dye adopts a fourth colour for temperatures higher than a temperature threshold within the range of 34.3° C. to 34.9° C.

Preferably, the dye adopts a fifth colour for temperatures higher than a temperature threshold within the range of 34.9° C. to 35.5° C.

Advantageously, the dye adopts a sixth colour for temperatures higher than a temperature threshold within the range of 35.5° C. to 36.1° C.

Preferably, the thermochromic layer contains a thermochromic pigment or a liquid-crystal mixture.

The application of different temperature ranges of colour response makes it possible to use the thermo-optical structures according to the invention in various embodiments, depending on the temperature of the environment and individual features of patients being subjected to the test. It is also possible to combine colour ranges in one test. The primary colours: red, blue and green, are the easiest to obtain. Assuming that red corresponds to the first and the fourth colour, blue corresponds to the second and the fifth colour, and green to the third and the sixth colour, all the ranges mentioned above can be achieved by the use of two types of thermo-optical detectors.

Preferably, the liquid-crystal mixture is in the form of microcapsules of mixture of thermotropic liquid crystals from nematic or chiral nematic group.

Preferably, the liquid-crystal mixture is chosen so that it provides a thermochromic response in the red colour range of light reflected selectively for the temperature range from above 32.5° C. to 33.1° C., in the primary green colour range of light reflected selectively for the temperature range from above 33.1° C. to 33.7° C. and in the primary blue colour range of light reflected selectively for the temperature range above 33.7° C. to 34.3° C.

Preferably, also the liquid-crystal mixture is chosen so that it provides a thermochromic response in the red colour range of light reflected selectively for the temperature range above 34.3° C. to 34.9° C., in the primary green colour range of light reflected selectively for the temperature range from above 34.9° C. to 35.5° C. and in the primary blue colour range of light reflected selectively for the temperature range from above 35.5° C. to 36.1° C.

Preferably, the thermo-optical detector is provided with an allergen layer accommodated between the securing layer and the adhesive layer, wherein the allergen layer contains at least one capsule filled with a substance selected from the group including a known allergen, a histamine solution and a neutral solution.

Preferably, the thermo-optical structure contains in the allergen layer at least two capsules filled with substances selected from a group including a known allergen, a histamine solution, a neutral solution, separated from each other by a length within the range of 5 to 7 cm.

Preferably, the thermo-optical structure is substantially rectangularly shaped, wherein its first side is not shorter than 3 cm, and its longer side is not shorter than 8 cm.

Preferably, on the screen there is applied at least one scale, especially carthesian or polar, composed of concentric circles.

According to the invention, a thermo-optical detector is used for evaluation of the extent of the skin allergic reaction to the test substance.

A recording device comprising a central unit, a housing adapted to separate a patient's skin region from the ambient light, a digital camera for acquisition of colours displayed on a thermo-optical structure in contact with the patient's skin, characterised in that it is provided with ambient temperature measuring means and patient's skin temperature measuring means connected to the central unit, and a standardized light source for illuminating the thermo-optical structure. Due to the application of standardized light source the achieved analysis of the image of the elevated temperature region visible on the thermo-optical structure is more precise. Furthermore, providing the device with ambient and skin temperature measuring means makes it possible, depending on thermal conditions, to display for the user the information which thermo-optical structure should be used, or information that the thermal conditions are unsuitable.

Preferably, the ambient temperature measuring means is an electronic thermometer, and the patient's skin temperature measuring means is a pyrometer providing a contactless measurement.

Preferably, the housing is internally covered with an absorbing layer.

Preferably, the standardized light source is a white LED having the Colour Rendering Index (CRI) value greater than or equal to 90.

Preferably, the recording device is provided with a radio communications interface, and the central unit is adapted to transmit the image from the digital camera via this interface to another device.

Preferably, the device is provided with an interface enabling connection of a portable memory, and the central unit is adapted to store in this memory the image from the digital camera.

Preferably, the device is provided with additional display means, and the central unit is adapted to output by means of it information identifying the thermo-optical structure from the set, the use of which will provide the best result in the thermal conditions identified by means of temperature measuring means. Due to this the combination of application of the device according to the invention with application of the thermo-optical structure according to the invention provides the quickest and the most precise diagnosis. The ambient temperature measurement in combination with the measurement of the patient's skin allows to evaluate what temperature range the temperature threshold of the dye in the used thermo-optical structure should fit into.

The method of diagnosing allergy according to the invention comprises
- the exposition step, wherein there is performed at least
  - exposition of the first region of patient's skin to histamine solution,
  - exposition of the second region of patient's skin to neutral solution,
  - exposition of the third region of patient's skin to test substance,
- measurement step, wherein the extent of histamine reaction is evaluated in at least the first, the second and the third region,
- comparison step, wherein the extent of histamine reaction in the third region is compared to the extent of histamine reaction in the first region and in the second region.

According to the invention the measurement step includes applying at least one thermo-optical structure according to the invention, to be put in contact with the patient's skin in the first, the second and the third region, wherein the extent of histamine reaction in the first, the second, and the third region is evaluated based on the extent of the change in colour of the thermo-optical structure inherent respectively for the first, the second, and the third region.

In the measurement step there can be applied a single thermo-optical structure having the area encompassing the first, the second, and the third region with a margin of width of at least 3 cm. It is also possible to apply individual thermo-optical structures for each of the regions.

Preferably, in the measurement step the largest dimension $S_T$ of the change in colour corresponding to the third region, the largest dimension $S_H$ of the region of the change in colour corresponding to the first region, and the largest dimension $S_N$ of the region of change in colour corresponding to the second region are subjected to measurement, with the assumption that the test substance is an allergen if the result of the operation $$\frac{S_T - S_N}{S_H - S_N}$$

is greater than or equal to 1.

Preferably, the measurement step is performed automatically by means of the recording device according to the invention.

Preferably, the exposition is performed by puncturing the patient's skin with a needle with the substance applied thereon.

Preferably, the exposition is performed by application of the substance on the skin.

The thermo-optical structure, the recording device, the application and the method understood according to the invention make it possible to replace the subjective visual method of evaluating the diameter of the epidermic erythema, which being only a symptom is treated as an indicator of the allergic reaction intensity. The epidermic erythema can be masked differently and it largely depends on the thickness of the epidermis layer, individual condition, or skin pigmentation, while the actual subcutaneous hyperthermia cannot be masked and is a result of histamine migration and the stimulated by it thermogenic effect related to the vasodilatory action on the microcirculation vessels. The extent of the vascular response to histamine is a direct marker of the rate and intensity of skin allergic reaction. Replacing it by the evaluation of the intermediate symptom in form of epidermic discolouration, i.e. redness, causes that the evaluation is not objective. However, the region of elevated temperature directly corresponds to the extent of the response to histamine.

The invention is based on dermo-thermal effect, and its relation to allergic reaction with respect to cellular mechanisms arises from this, that the direct signal for degranulation of grains and histamine ejection is the binding of antigen-allergen to specific antibodies located on the surface of mast cell's cell membrane, the key role played here by the superficial receptor FcεRI binding IgE class antibodies. The extent of the epidermic reaction in the form of erythema induced by the released histamine is proportional to the degree of allergic reaction intensification, therefore it constitutes one of the markers of intensity of skin allergic reactivity.

DESCRIPTION OF THE DRAWINGS

The object of the invention has been depicted in embodiments on the drawings, wherein FIG. 3 is a table showing the relation between temperature and wavelength for liquid-crystal mixtures applied in an embodiment of the invention, FIG. 4 is a table including exemplary ranges of thermochromic response in the range of primary colours for liquid-crystal mixtures in an embodiment of the invention, while FIG. 5 is a table including exemplary compositions of these mixtures.

DESCRIPTION OF EMBODIMENTS

The basic function of a thermo-optical structure according to the invention is the conversion of thermal biological signal, falling within the infrared range, with electromagnetic wave length from 8 µm to 15 µm, generated under the skin in result of vasodilatory thermogeneous histamine reaction, into colour image of temperature distribution on the surface of skin, in the spectral range of visible light with wavelength from 380 to 780 nm.

The thermo-optical structure according to the invention functions as an intensifier for the image of subcutaneous hyperthermia induced by histamine during the allergic reaction, because of that the local skin temperature increase is associated with a corresponding colour of light selectively reflected in the thermochromic dye layer or in thermotropic mesophase forming the system's screen, and preferably the respective primary colours red, green, blue appear sequentially at every 0.6° C.

To cover the typical spectrum of temperatures present on human skin with a set of primary colours it is purposeful to provide a set of thermo-optical structures according to the invention with temperature thresholds of colours distributed at every 0.6° C. or denser, in the range of 31° C. to 37° C.

A physician can select a system suitable for a patient in given conditions based on the skin temperature measurement or matching them in sequence.

A preferable solution is to provide two thermo-optical structures turning into 3 colours. Therefore, each of them covers a larger range of temperatures. The first thermo-optical structure operates in the range of 32.5° C. to 34.3° C. The second thermo-optical structure operates in the temperature range of 34.3° C. to 36.1° C. This solution allows to conduct an allergy test on most patients by means of one of the two thermo-optical structures in a set.

Figure 1:
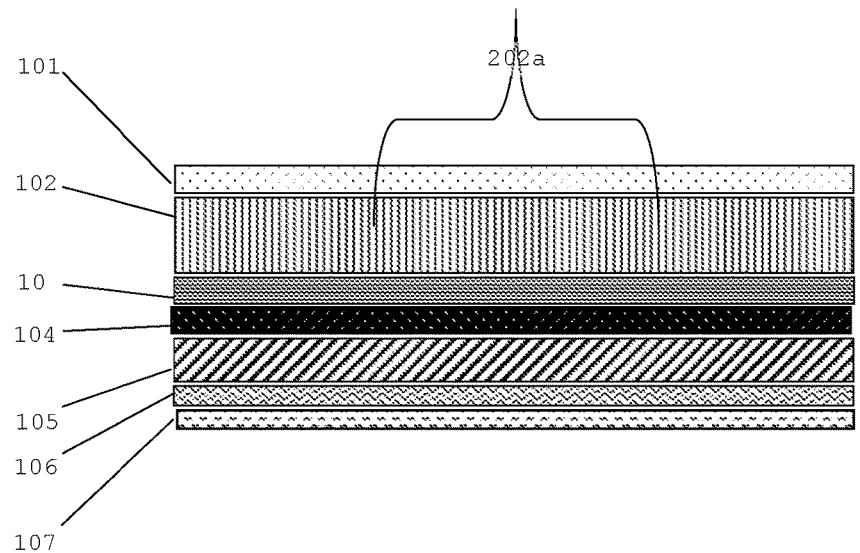
FIG. 1 is a schematic cross-section of the test according to the invention with individual layers marked.
Figure 2:
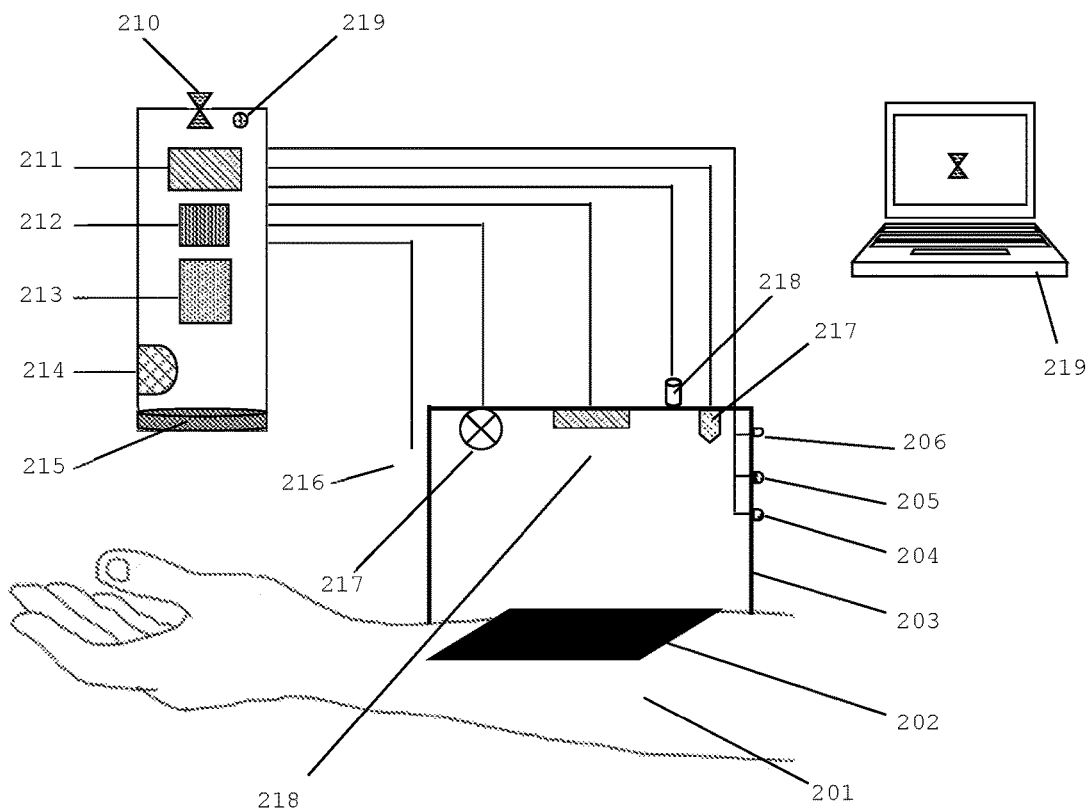
FIG. 2 is a block diagram of the system according to the invention.

The thermo-optical structure according to the invention has a layered structure shown in FIG. 1. The layer 102 of a transparent film is constituted by a transparent base film made of polyester, wherein also a screen 102a is provided. The layer 102 of the transparent film is a carrier for the thermochromic layer 103 comprising a thermochromic dye present in the form of a mixture of micro-encapsulated thermotropic liquid crystals from the nematics group, especially chiral nematics. The thermochromic layer 103 is covered by a polymer with the addition of a black dye acting as an absorber. This polymer constitutes an absorber layer 104.

If the layer of liquid-crystals applied on a transparent thermo-optical film is not covered with a black dye acting as an absorber, then the colour of light reflected selectively in the thermotropic mesophase is visible directly on the background of the examined skin of the patient, leading to a much smaller contrast, and thus the boundaries of the image of the hyperthermal erythema, essential for reading out the allergic test, can be blurry, however such thermographic image is applied directly on the location of conducting the allergic test, which is then visible for the physician, and the application of the thermo-optical structure anyway provides an improvement in accuracy with respect to the currently known tests.

The layers 103 of the dye and 104 the absorber are secured by a securing layer 105 made of thin polyethylene or polypropylene film separating it from the layer of adhesive.

The layered structures with the following layer configuration: transparent film layer 102, thermochromic 103, film 105 with an optional absorber layer 104, are known in the state of the art in various applications. They are commonly referred to as a thermo-optical foil.

On the securing layer 105 there is applied an adhesive layer 106. The adhesive applied in the adhesive layer is biologically and chemically neutral for human skin. Additionally, the thermo-optical structure is provided with a protective layer 107 made of impregnated cellulose film. This layer can be easily peeled from the adhesive layer 106 directly before the application of the thermo-optical structure on the skin.

On the external surface of the polyester base film layer 102, on the side of the screen window, there is applied an optical filter layer 101—chemical or physical. Such filters are available on the market and manufactured e.g. by Koshin Kogaku Co., Ltd. Japan, or Edmund Optics Inc., USA. The filter layer 101 serves to eliminate the spectrum of electromagnetic waves in the wavelength range of 589 to 700 nm, thus red light. Therefore the contrast of the thermochromic response below 589 nm, in the range of green and blue-violet colour, increases. Thus an additional Improvement of readout accuracy is obtained.

Alternatively, other spectral ranges can be filtered. For example, using an optical filter (1) eliminating the spectrum of electromagnetic wave in the wavelength range of 400 to 500 nm, i.e. the beam of selectively reflected blue light, and increasing the contrast of the thermochromic response above 500 nm, in the range of green and red colour.

The kind of filtration is selected based on the used liquid-crystal composition, and more precisely, on what colour range these crystals provide a response to temperature change. The Increase of the contrast is obtained through elimination of the portion of visible light spectrum which does not correspond to the applied colour response range.

The allergen for allergic reaction test is usually Introduced by puncturing the skin with a needle, which has been previously wetted by the allergen. Then the geometric centre of the allergic reaction focus substantially corresponds to the spot of puncture. Analogically the histamine and neutral solutions are handled. Usually the tests are performed at once for more than one allergen. The patient is subjected to a series of punctures arranged in a row or a matrix on a forearm or on the back. The separation of punctures is chosen so that the erythemas of adjacent tests do not overlap. In case of thermal tests the typical separation should be increased by at least 5 cm. For observation of the region around the puncture at least a circular area with radius of 3 cm should be preserved.

The readout of skin reaction to allergen in point or scarification tests occurs not sooner than 15 minutes after the moment of application. For readout the thermo-optical structure according to the invention is adhered directly on patient's skin in the location of conducting the allergic tests, on the side covered with adhesive layer 106, after previous peeling of the protective film layer 107. After the minimum of 10 seconds from the moment of adhering the thermo-optical structure onto the examined skin in the window forming the screen 102a there appears or not a colour image of focal hyperthermia as an indicator of histamine reaction intensity, and thus the existence of allergy for the given allergen. Depending on the number of expositions, one or more thermo-optical structures can be used. In particular, Independent systems can be used for each change.

The image of the induced hyperthermia during an allergic reaction is of green or blue colour in the screen, because of the application of the optical filter eliminating red colour on the film I operating in the range of 32.5° C. to 34.3° C., or is of green or red colour in the screen, because of the application of an optical filter eliminating blue colour on film II operating in the range of 34.3° C. to 36.1° C.

In the preferred embodiment, the thermo-optical strip system according to the invention has the size corresponding to such matrix or row of punctures and is provided with a large screen, or in a matrix or a row of screens 102a, which correspond to respective punctures. This solution can be improved by providing in the centre of the screen an aperture for puncturing with a needle dipped in an allergen. Then, the procedure of puncturing is performed after the application of the thermo-optical structure according to the invention on patient's skin, so that the screens and the punctures correspond each other accurately.

An additional preferable modification of this embodiment of the thermo-optical structure is providing a scale located on the screen. This can be a millimeter scale, enabling an easy readout even when the centre of a puncture and the centre of the scale displace with respect to each other. Also, a scale in the form of concentric circles can be used. Such solution has the advantage, that it facilitates the readout and allows to immediately evaluate the extent of allergic change even if the thermal spot has irregular shape. However, its disadvantage is that if the centre of the scale becomes displaced with respect to the centre of the change its usefulness diminishes drastically. Providing more than one scale on the screen allows to simultaneously examine a greater number of readouts.

The process of examination can be shortened significantly by using the following improved embodiment of the invention. In this example an additional allergen layer is provided. The best results come from arranging it between the securing layer 105 and the adhesive layer 106, i.e. as close as possible to the patient's skin, the allergen layer covered in points with microcapsules containing inside a selected allergen or typical set of allergens and substances for conducting the control test: a neutral solution and pure histamine. The diameter of the microcapsules is 12 mm. Geometric centres of the microcapsules correspond to centres of the screens. The securing layer 105 constitutes then a carrier for allergens used for examination of the contact allergy.

The test is conducted by application of the thermo-optical structure on the skin, and next strong pressing at locations where micro-encapsulated allergens are situated, causing their gradual release onto the surface of the skin. Therefore the allergens can be used for production of analogues of contact allergy tests, and the mechanical pressure within the range required to release the allergens from the microcapsules does not affect the quality of thermochromic response of the mesophase.

A more precise result can also be obtained by puncturing with needles through the whole thickness of the system at points where the microcapsules are located, leading to the typical method of allergen application, carried out by puncturing the skin with a needle covered with the allergen. In this method of application the size of a micro-capsule can be smaller, even below 1 mm.

Numerous technologies of producing thermo-optical film with elastic transparent polymer, constituting a carrier for a thermochromic layer comprising thermotropic liquid crystals from chiral nematics or non-chiral nematics group, preserved against mechanical distortion by micro-encapsulation, are known to the persons skilled in the art. This is related to numerous industrial applications of this kind of films, inter alia for production of thermometers. Such solutions have been disclosed inter alia in U.S. Pat. No. 6,204, 900, 1997, wherein the invention entitled "Microencapsulated liquid crystal and a method and system for using same" has been disclosed, No. U.S. Pat. No. 6,120,701, 1999, wherein the invention entitled "Microencapsulated liquid crystal and a method and system for using same" has been disclosed, or in the newest application US20130146811, 2012, wherein the invention entitled "Method of reusing micro-encapsulated cholesteric liquid crystal" has been disclosed, all of these have been included in the present specification by reference. Because of this it is reasonable to make use of the commercial offer of industrial micro-encapsulation of liquid crystals from the nematics group, including chiral nematics, with the use of suitable organic polymers, as well as of the offer of production of suitable liquid-crystal blends having narrow given range of thermochromic response of mesophase, e.g. of the company LCR Hallcrest, USA.

In an embodiment there is provided a set of thermo-optical structures according to the invention, which ensure coverage of the typical temperature spectrum, with the use of two different mixtures of thermotropic liquid crystals from the nematics group, including chiral nematics, characterised by thermochromic responsiveness in two required operation temperature ranges, the first of 32.5° C. to 34.3° C. and the second of 34.3° C. to 36.1° C., with relatively constant thermo-optical separation of both mixtures for primary colours: red, green, blue, having the width of 0.6° C.

In the table shown in FIG. 3 there is shown the relation between the temperature $T_n$(° C.) and electromagnetic wave length of light reflected selectively $\lambda_n$(nm) in thermotropic mesophase, measured spectrophotometrically for mixture I responsive thermo-optically in the range of 32.5° C. to 34.3° C. and mixture II responsive thermo-optically in the range of 34.3° C. to 36.1° C., composed of liquid crystals from the chiral nematics group, including non-chiral nematics.

In the table shown in FIG. 4 there are shown the temperature ranges of thermochromic response in the range of primary colours: red, green, blue for mixture I responsive thermo-optically in the range of 32.5° C. to 34.3° C. and for mixture II responsive thermo-optically in the range of 34.3° C. to 36.1° C., composed of liquid crystals from the chiral nematics group, including non-chiral nematics, simultaneously defining as 0.6° C. the thermal width of individual ranges, where respective primary colours of light reflected selectively in mesophases of both mixtures appear.

The examples of mixture I responsive thermo-optically in the range of 32.5° C. to 34.3° C., mixture II responsive thermo-optically in the range of 34.3° C. to 36.1° C. composed of liquid crystals from the chiral nematics group, including non-chiral nematics, have been presented in the table shown in FIG. 5 defining qualitative and quantitative compositions of both mixtures, genera qualitative compositions. Such mixtures are known inter alia from the US patent documents U.S. Pat. No. 3,441,513, U.S. Pat. No. 4,301,023, U.S. Pat. No. 5,508,068, U.S. Pat. No. 4,547,309, and from the European application No. EPO404639. There are also known commercial suppliers of mixtures realised according to customer's requirements. For example, the company LCA Hallcrest, USA, based on characteristics of thermochromic response included in the table shown in FIG. 3 is able to supply prepared mixtures.

For example, the base film layer 102 is made of transparent polyester having the thickness about 120 μm. The mixture of liquid crystals from the nematics group, including chiral nematics, micro-encapsulated by MELC (Micro-encapsulated Liquid Crystals) technology, having the sphere diameter about 30 μm and comprising at least 5 liquid-crystal fractions, to form the thermochromic layer 103 having the thickness about 40 μm, is applied on the base film layer 102 by means of screen printing, previously suspending the microcapsules in a suitable polymer dispersion usable in screen printing technology, with the use of organic solvents neutral with respect to chemical compounds the micro-spheres are made of, the composition of the dispersion and selection of solvents are prepared by the micro-encapsulation supplier.

The thermochromic layer 103 with micro-encapsulated liquid crystals is covered in screen print with an additional polymer absorbing layer 104 comprising a black dye, with the use of reagents produced by Pröll KG, the base Norilit® 100 OXY with the addition of black dye 948 Black and 10% solvent Thinner 190, drying through solvent evaporation in temperature of 20° C.

The application in the device according to the invention of mixtures of liquid crystals from the nematics group, including chiral nematics, suitably selected with respect to additions, allows to obtain a clear thermochromic response of the mesophase in form of the phenomenon of selective reflection of beam of light with a defined electromagnetic wave length, which occurs always in particular predefined temperature ranges. This allows to calibrate properly the whole device at the thermo-optical structure production step and obtaining repeatability of readouts.

Therefore, a physician evaluating the results of skin allergic tests of a patient will be certain, that each time the result of the allergen tests will be standardized due to imaging the subcutaneous histamine-induced hyperthermia and with respect to control conducted on standard basis with the use of a reference 1 mg/ml histamine solution, such comparison of reactions allows to evaluate the individual relative extent and intensity of the allergic response.

Typically a patient is a human, and the tests are conducted on the internal side of a forearm or on the back. Because of the use of a transparent base film without absorber the changes on skin can be simultaneously observed, however on a cost of the contrast.

A person skilled in the art also knows methods of obtaining the technical effect of selective reflection of light wave under the temperature change other than liquid-crystal mixtures. This effect can be obtained, for example, by the application of suitable chemical compounds included in the group of reversible thermochromic dyes, described inter alia in patent documents: U.S. Pat. No. 5,480,482, U.S. Pat. No. 5,558,700, U.S. Pat. No. 4,720,301, U.S. Pat. No. 5,219,625, U.S. Pat. No. 5,558,700, U.S. Pat. No. 5,591,255, U.S. Pat. No. 5,997,849, U.S. Pat. No. 6,139,779, (U.S. Pat. No. 6,494,950), U.S. Pat. No. 7,494,537, U.S. Pat. No. 7,332,109, U.S. Pat. No. 6,485,824, EP2138550, or irreversible, described inter alia in patent documents: US20140037362, U.S. Pat. No. 7,278,369, US20090278090, WO1984000608, US20050104043, included in the present specification by reference.

Alternatively, by the use of the suitable stabilized thermotropic liquid crystal mixtures, the thermo-optical activity of which is a result of their macro-structure and not the property of individual particles, and in this aspect, the thermo-optical effect is obtained in a completely different mechanism than in the case of non-liquid-crystal thermochromic dye, in particular applicable are liquid crystals from the nematics group, including chiral nematics, characterised by the ability to reversible change of the wavelength of light reflected selectively in their mesophase with the change of temperature, and where the selective reflection corresponds to the Bragg-like effect, described by the formula known from literature:

$$\lambda_0 = n_{avg} p \left[ \cos \frac{1}{2} \left\{ \sin^{-1}\left(\frac{1}{n_{avg}} \sin\varphi_i\right) + \sin^{-1}\left(\frac{1}{n_{avg}} \sin\varphi_s\right) \right\} \right]$$

where:

$$n_{avg} = \frac{2n_{o,ch} + n_{e,ch}}{3}$$

$\varphi_s$—is the selective reflection angle.

The changes occurring in the thermotropic mesophase formed by liquid crystals from the nematics group, including chiral nematics, under heating make it possible to precisely transform the invisible for human eye thermal signal from the range of 32.5° C. to 36.1° C., into the colour image of isotherm distribution on the surface of the examined skin, appearing in the visible spectrum range of electromagnetic wave length of 380-780 nm.

In case of thermotropic liquid crystals from the nematics group, including chiral nematics, there is a possibility of precise programming the ranges of selective reflection in the mesophase of the monochromatic components of white light in function of temperature, according to known methods of doping individual components to liquid-crystal blend, as described in scientific literature, e.g. by Kwang-Soo Bae et al. ("Wavelength-Selective Reflection of Cholesteric Liquid Crystals Depending on Temperature and Dopant Concentration", Proceedings of the 16$^{th}$ International Display Workshop, 2009), and S. Y. T. Tzeng et al. (Thermal tuning band gap in cholesteric liquid crystals, Liquid Crystals, Vol. 37, No. 9, 2010).

The thermo-optical structure according to the invention serves to intensify the image of the histamine reaction, and precisely of the hyperthermia induced by local histamine release, which causes an erythema, in response to the introduced allergen corresponding to the conducted skin provocation allergic test, causing the visualisation of the actual subcutaneous diameter of this erythema in the thermographic image, and the extent of which can be read out on a millimeter scale directly at a passive screen of thermographic converter, replacing the previously used method of epidermic reaction extent measurement. Preferably, the contact thermo-optical converter according to the invention eliminates the problem of subjective erythema intensity evaluation by determination of its boundaries based on skin colouration, because the colour of skin does not impact the infrared radiation emissivity, while the visible light, in the range of radiation with wavelength of 380-780 nm, is reflected in 30-40% by white skin and in 18% by black skin. Therefore, skin pigmentation can cause artificial reflection of the allergic erythema in visible light for patients having black skin, making the readout unclear, however it does not influence the thermographic image, the device according to the invention eliminated also this drawback of the visual skin allergic test readout.

To determine the diameter of erythema visible in the thermo-optical film's screen it is necessary to identify the largest focus or foci with the colour corresponding to the highest registered temperature and measure its diameter in millimeters, analogously as in the case of reading out the epidermic erythema, or to use a function of automatic measurement available in an adapter recording the thermographic image. The focus corresponding to the hyperthermal erythema can appear red on black background in the screen's window, then the temperature differential between the interior of the focus and the thermal background generated by healthy adjacent skin is 0.6° C., if the colour of the focus is green, then similarly the determined temperature differential is 1.2° C., and if the colour of the focus is blue, then similarly the determined temperature differential is 1.8° C.

An additional improvement of readout accuracy and test precision can be obtained by using a recording device, or so-called optoelectronic colour digital image recorder, operating in the visible light range, with electromagnetic wave length of 380 to 780 nm. In the present embodiment, the recorder is composed of a parallelepiped housing, closed from 5 sides, covered in the inside with a black matte coating, restricting the access of the ambient light. Furthermore, it is provided with a digital camera with CCD (Charge Coupled Device) or CMOS (Complementary MOS) type optoelectronic converter and an optical objective having the focal length of about 2.8-12 mm, for recording the test result in a form compatible to requirements ISO/IEC 14496 on an external flash memory type storage medium connected to a communications port in USB (Universal Serial Bus) standard. Further, the recorder is provided with an alphanumeric-graphical liquid crystal or amoled display. A feature of the recorder is a standardized white light source illuminating the interior of the housing in the spectral range of electromagnetic wave lengths of 380-700 nm obtained from wide-emission LEDs. The recorder operates under the control of a CPU (Central Processing Unit) microprocessor controlling its sub-circuits, and for processing graphics it comprises a distinct GPU (Graphic Processing Unit). The executed programs are stored in operational RAM having the size of 8 GB. The recorder enables preliminary digital test image analysis, including overlaying on the image a virtual digital orthogonal millimeter grid with a unit cell of 1 mm per 1 mm, and a measurement of the hyperthermia image diameter.

Providing the recorder with a wireless transmitter, preferably according to the standard described in specification IEEE 802.15.1, allows for a more convenient handling.

Additionally, the recorder is provided with an electronic thermometer 216 for measuring external temperature in the range of 0° C. to +40° C., a pyrometer 207 making it possible to measure remotely skin temperature in the range of 28° C. to 42° C.

The power source is a rechargeable battery with the operational voltage of at least 3 V.

The user interface comprises a switch making it possible to turn on and off the device, the test button, an optical turn-on and ready-state indicator in both acoustic and optical (green LED) form and completion indicator in the form of a blue LED.

Reading out the results of a skin allergic test conducted by means of a thermo-optical structure and a recording device according to the invention is carried out not by determination of the thermal value of the hyperthermal focus, but according to the current clinical standard, by measuring its extent, and more precisely, the average diameter in millimeters.

The process of the test is as follows. The housing of the recorder is put in contact with the skin in the test location and initial temperature analysis is conducted.

For verification of thermal condition properties an electronic thermometer embedded in the recorder is used, which measures the ambient temperature, and a contactless pyrometer for measuring the temperature of the patient's skin surface.

The verification is conducted by putting the open end of the thermo-optical recorder into contact with the skin region where the skin allergic tests were conducted, and pressing the "test" button.

The verification takes 5 seconds and if proper conditions for test conduction are confirmed by measurement, the green LED lights on.

Based on the skin temperature the proper thermo-optical structure from the set is determined. The information of the test selection is displayed for the user by indication on the display and a colour diode. In case of threshold temperature value, the selection is determined by the ambient temperature value.

Next, a thermo-optical strip system according to the invention, after peeling the protective layer 107, is applied onto the patient's skin. If a system without allergen capsules is used, then the skin should be previously punctured with the tested allergens with at least 5 cm intervals, and carry out at least one puncture with a neutral solution, e.g. NaCl 0.9%, as a neutral test, and one puncture with histamine solution, e.g. 1 mg/ml, as a control histamine test. If a system with an allergen applied externally is used, then the allergen should be applied onto the skin by strongly pressing the system against it. If the embodiment with punctured capsules is used, after adhering the test it should be punctured in the locations of placement of the allergens and the solutions with a sterile test element to the depth ensuring puncturing the epidermis below.

The thermo-optical recorder is again put in contact with the open side to the patient's skin at the location of examination, where this time there is adhered the thermo-optical structure, optimally in time of up to 10 seconds from the moment of adhering the film, after pressing the start button, a sequence of calibration and repeated verification of thermal conditions is initiated, if these conditions are satisfied, the green LED lights on and the recording of thermographic image of the skin allergic tests results begins, the blue LED lights on, informing about the start of image recording, next, after 15 seconds, the recording control processor provides an acoustic and an optical signal (the blue LED lights off), the readout is finished and the result has been automatically stored on the flash memory card and sent wirelessly to a computer connected via Bluetooth interface.

The readout of the allergic reaction result in association with the conducted skin provocation test is carried out directly on the screen of the thermo-optical film by measuring, in millimeter scale, the hyperthermal focus diameter, visible in a colour corresponding to the highest temperature recorded by the device.

The results of the skin allergic test by means of the device according to the invention are read out after at least 20 seconds from the moment of the application of the thermo-optical film on the examined skin, but not later than after 1 minute, because of limited thermal capacity of the device.

The GPU (Graphic Processing Interface) processor runs an additional program, overlying a virtual millimeter grid onto the image of all the hyperthermal foci recorded in a single measurement sequence and executes the measurement of average diameter in millimeters of each focus, and finally displays on the display an "OK" sign, informing about correct completion of the recording of the test, if any of the recording operations has failed, an error message "ERROR" is displayed on the display, then the whole test should be repeated using a new thermo-optical structure for this purpose.

If the computer has not been previously connected wirelessly with the thermo-optical recorder, to load the image of the test into the computer the flash memory card can be ejected from the digital camera incorporated in the recorder and load the results directly from this memory.

Proper thermal conditions have to be satisfied for a correct readout of the results of point or scarification skin allergic tests by means of the device according to the invention.

The proper thermal conditions for conducting a readout are determined by: ambient temperature within the range of 21° C. to 27° C. and the temperature of the examined skin within the range of 31° C. to 37° C.

If the proper thermal conditions are not confirmed, the red LED lights on, the measurement should be then repeated with the use of a new and/or different thermo-optical structure, and possibly conduct the tests in other room, if the device indicates that the ambient temperature is improper.

The readout of the result of skin allergic tests is conducted based on calculated average diameter of the recorded hyperthermal focus, according to the formula:

$$R_{av} = \frac{R_{max} + R_{min}}{2}$$

where:
$R_{av}$—is the average hyperthermal focus diameter in millimeters,
$R_{max}$—is the hyperthermal focus diameter in millimeters, measured along the major axis,
$R_{min}$—is the hyperthermal focus diameter in millimeters, measured along the minor axis, perpendicular to the major axis.

A program automatically indicates the geometric centre of the elevated temperature focus, by determining the point (pixel) of maximal temperature (point $T_0$) and it corresponds to the point of puncture and allergen introduction. The average increase in temperature $\Delta T$ in a ring with radius r is determined in the range: $n \times Dr \pm Dr/2$ (where n=0, 1, the program identifies step Dr equal to the pixel size, and the radius of change is identified up to the moment, when the temperature increase value reaches the value of maximal measurement error. The maximal error of the thermographic measurement dT is assumed to be equal to the maximal temperature differential possible to identify in the thermographic image at thermo-optical resolution of 0.6° C., thus with no filter in the system of 3 primary colours: red, green, blue, it is: 3×0.6° C.=1.8° C., and with applied optical filter removing red or blue colour: 2×0.6° C.=1.2° C.

In scientific literature it is assumed that for skin allergic tests evaluated visually a reaction in form of erythema with diameter of at least 30 mm or more is considered symptomatic, wherein the researchers Bernstein I. L., Blessing-Moore J., Cox L. S., Lang D. M., Nicklas R. A., et al., (Allergy Diagnostic Testing: An Updated Practice Parameter: Ann. Allegry, Vol 121, 8, 2008) emphasize that the erythema can be, except of serous blister, an independent measure of bioequivalency of skin tests, this means, that the diameter of erythema identifies the presence of allergy of the patient for the tested allergen.

The extent of the hyperthermal reaction revealed after conducting an allergy test is individually specific, regardless if the readout is based on the epidermic erythema, or on the subcutaneous reaction and employs thermography, therefore the measured diameter of hyperthermal focus should be related to the extent of the control test with histamine with the concentration of 1 mg/ml.

The hyperthermal readout pronounced less than the control test with histamine by ca. 50% indicates also a positive result with indication of weaker allergic effect, and the readout pronounced by ca. 20% less than the control test is inconvertible or is artefactual and cannot unambiguously indicate the allergy to the specific allergen.

The histamine-induced expansion of vessels generates hyperthermia, which is a thermodynamical marker of allergic reaction, detected by the apparatus according to the invention, as mentioned, histamine causes an additional heat source to appear in the subcutaneous tissue ($Q_R$), the power of which is proportional to the concentration of histamine and described by the formula:

$$Q_R(r, t) = \Delta Q_0 c_H\left(r, \frac{r}{v}\right) = \Delta Q_0 c_{OH} \exp\left(-\gamma \frac{r}{v}\right) = \Delta Q_0 c_{OH} E(\gamma)$$

where:
$\Delta Q_0$—is a positive constant,
$c_H$—is the tissular histamine concentration, with the assumption that:
$C_{H(0,0)} = C_{0H}$
$v$—is the velocity of histamine migration in the skin,
$\gamma$—is the tissular histamine elimination rate, Low values of thermal conductivity coefficient cause that heat diffusion from the point source of histamine introduction (for control test) by thermal conduction is negligible (max. $\Delta T \sim 0.2°$ C.), therefore it is assumed that the extents of the region of elevated temperature measured on the skin surface is determined by the extent of the heat source arising due to the increased blood perfusion, enforced by vasodilation caused by the histamine diffusing in the subcutaneous tissue. Thus, the heat source appears in the point (r) of conducting the control histamine test, after time t:

$$t = \frac{r}{v},$$

The increase of the heat is constant in time and depends linearly directly on the maximal tissular histamine concentration at point r. Assuming, that the energy generated by metabolic processes is close to zero, the following equation for temperature distribution is obtained:

$$\frac{d(\Delta T)}{dt} + \tau \Delta T = S_H$$

where:
$S_H$—is the tissular histamine concentration,
With satisfied boundary condition: $\Delta T(r,0)=0$ and wherein:

$$\tau = \frac{1}{\rho c_{sh}}(\omega \rho_b c_b + \alpha)$$

$c_{sh}$—is the specific heat of skin,
$\rho$—is the density of skin,
$\omega$—is the blood perfusion,
$c_b$—is the specific heat of blood,
$\alpha$—is the heat transfer coefficient.

Assuming that the temperature of blood is a constant value, and also that the ambient air temperature is a constant value, according to the above presented formula $Q_R$ denotes the histamine-induced heat source appearing due to expansion of vessels, then the solution of the temperature distribution equation is:

$$\Delta T(r,t) = \frac{S_H(r)}{\tau}(1 - e^{-\tau t}).$$

This is the known from the literature of the subject the biophysical theoretical description of propagation of heat generated in histamine-induced vasodilatory effect in a model of allergic reaction which is the basis for implementation of analysis of test results in the recording device according to the invention or in an external computational unit, to which the image from the recording device is provided.

Taking into account the effect of direct heat conduction to the thermo-optical structure, attempting read out the result of skin allergy tests to correctly with the use of the recording device according to the invention, the attention should be paid to accurate adhesion of the thermo-optical structure to the whole surface of the examined skin, for this purpose serves coating it at the bottom side with an additional adhesive layer 106, e.g. supplied by the company 3M, comprising the same or similar adhesive to the one used in medical patches. The use of this adhesive also requires to protect it with a protective layer, i.e. a peeled impregnated cellulose protection 107

The thermo-optical structure used for evaluation of result of point or scarification skin allergic tests is disposable for two reasons. First, a perfect contact of the system with the examined region of patient's skin has to be provided, thence the use of the adhesive layer 106. Second, residues of the tested allergen can remain thereon, and also residues of body fluids of the patient, coming from an infiltration or exudate, constituting an irremovable biological contamination.

A negative result of a skin allergic test is always indicated by no reaction in the form of erythema and no infiltration in the form of a serous blister, therefore, due to high sensitivity of the thermographic device, each erythema visible in the screen indicates a less or more intensified hyperthermal post-histamine reaction and is an indicator of allergic reaction. However, because of the individual variation of allergic response intensity, the description of a result for a given allergen is always provided in millimeters and it should always be related in comparison to the result of control with the use of pure histamine solution.

The recommended set for allergic reaction testing is composed of two thermo-optical structures, each with a different range of operational temperatures, because in empirical research at least two groups of patients have been distinguished, which are characterised by a different rate of tissular histamine perfusion, the higher ca. 0.045±0.004 mm/s, and the lower ca. 0.015±0.008 mm/s, in consequence also a different degree of intensity of allergic reaction, and, related with it, also a different scale if Induced hyperthermia. Additionally, during construction of the recorder according to the invention the age of the patients has been taken into consideration, for older patients, aged 60 or more, it is recommended to use the first film, operable in the range of lower temperatures of 32.5° C. to 34.3° C., to determine the extent of the hyperthermal reaction accompanying the skin allergic reaction with lower intensity. The second thermo-optical structure, providing a thermochromic response in the range of higher temperatures of 34.3° C. to 36.1° C., is recommended for use for young persons, in particular children, and for the case of selection of a forearm as the location of conducting the skin allergic test, because in this location a higher average skin temperature is observed than in the case of conducting the test on the back.

Preferably, the recorder based on the indications of the thermometer 216 and pyrometer 207 determines the recommended temperature thresholds and on this basis displays the thermo-optical test system of the set recommended for the patient. Such solution can be applied also for sets comprising more than two thermo-optical structures.

The uniqueness of the solution used in the invention consists in the application of the discovery of the dermothermal effect, relating the focal hyperthermia present during skin allergic reaction to the allergic reaction intensification, measured by the scale of histamine release from the effector cells and the extent of its tissular migration, conditioning biophysically the extent of the area of elevated temperature caused by expansion of the microcirculation post-capillary vessels, mainly in subpapillary plexuses, for evaluation of provocation tests result.

The device according to the invention comprises an operational memory, to which there is loaded a program the operation of which is based on scientific background determining the model of histamine diffusion in skin layer, inducing vascular hyperthermia, assuming, that the intratissular heat source appears at point (r) after time (t) equal to $t=r/\upsilon$, and the heat increase is constant in time and depends linearly on the reached maximal histamine concentration, spreading from the source of allergen introduction. However, biophysical activation of heat source requires certain threshold value of tissular histamine concentration ($c_{TH}$), after crossing of which a cascade of biochemical processes leading to local expansion of micro-vessels starts. The maximal value of the radius (r) (denoted as: $R_a$) for the histamine concentration $c_H = c_{TH}$ can be determined using the formula:

$$R_a = \frac{\upsilon}{\gamma}\ln\left(\frac{c_{0H}}{c_{TH}}\right)$$

Based on the theoretical model, it can be noticed that the radius of hyperthermia increases linearly in time (with fast migration $\upsilon$), until reaching the maximal radius $R_a$, an in turn the temperature distribution on skin surface $T(r,t)$ is described by the known in literature Pennes equation for heat transport in biological tissue. The model correctly maps the experimentally recorded temperature distributions and allergic erythema extent, and because the value of skin thermal conductivity coefficient (λ) is much lower that the product of specific heat of skin ($c_{sh}$) and its average tissular density (ρ), it can be assumed, that, from the biophysical point of view, the heat transport by conduction in the skin is neglected, so that the direct heat source in this case is the increased perfusion of blood in the network if subcutaneous vessels activated by histamine during allergic reaction.

The dermo-thermal effect, associated to the histamine reaction, has been used for development of innovative and non-invasive thermo-optical structure according to the invention, operating as a thermo-optical converter and image intensifier of the actual hyperthermia accompanying the allergic reaction and applying the discovered during empirical studies two three-range colour-thermal detection scales, by means of which the evaluation of results of skin allergy tests is done, with specific population conditions taken into consideration.

In the exemplary method of diagnosis according to the invention, the greatest dimension $S_T$ of the region of colour change corresponding to the test with the examined allergen, the greatest dimension $S_H$ of the region of colour change corresponding to the histamine test, and the greatest dimension $S_N$ of the colour change corresponding to the test with neutral solution NaCL are subjected to measurement. It is assumed that the test substance is an allergen if the result of the operation $$\frac{S_T - S_N}{S_H - S_N}$$

is greater than or equal to 1.

The application of the device is particularly important for clinical practice, for obtaining an objective diagnosis of allergy, especially for patients with exceptionally strongly or weakly pronounced skin reaction. Attenuation of reactivity is frequent by diagnosing older persons (M. J. King et al. "Allergen prick-puncture skin testing in the elderly", Drugs and Aging, 2003), because the reactivity to allergen decreasing with age is observed in population, due to, inter alia, decreased tissular effectiveness of histamine perfusion. During empirical research two groups of patients have been distinguished, characterised by a higher value of histamine migration velocity of about 0.045±0.004 mm/s, and a lower value of about 0.015±0.008 mm/s. The range of variation of the histamine perfusion parameter during allergic reaction, additionally negatively correlated to age, proves the rationality and high effectiveness of the application of two three-range thermo-optical films used in the device according to the invention, what can be especially significant in diagnosis of patients aged above 60.

It is obvious that for a person skilled in the art, after the lecture of the above documentation and familiarising oneself with the invention and with the embodiments illustrating it, further alternative embodiments are evident. Thus, the mentioned embodiments do not limit the scope of the invention, defined by the patent claims, but serve only for illustration and exemplification.

The invention claimed is:

1. A method of diagnosing skin allergic reactions induced by in vivo skin prick test (SPT) and skin patch test (PT) and by identification of hyperthermic allergic responses, the method comprising the steps of:
    applying respectively on a first region, a second region, and a third region of patient's skin:
        a positive control histamine solution having a minimum concentration of 1 mg/ml to obtain a positive control reaction,
        a negative control sodium chloride (NaCl) solution having a concentration of 0.9% to obtain a neutral or negative control reaction, and
        a standarized testing allergen solution to induce allergic skin responses to evaluate allergic reactions;
    measuring hyperthermic reactions in the first, second and third regions by identification of hyperthermic areas displayed on a screen of a planar thermosensitive detector; and
    comparing a size of the positive control reaction (histamine-induced hyperthermia in the first region) with a size of the neutral or negative control reaction (sodium chloride-induced hyperthermia in the second region) and a size of the allergic reactions (allergen-induced hyperthermia in the third region),
    wherein the comparing step is performed based upon an extent of color images displayed, in the measuring step, on the screen of the planar thermosensitive detector, said displayed color images being relevant to the hyperthermic areas revealed over patient's skin in the first, second and third regions.

2. The method according to claim 1, wherein the measuring step is performed automatically by means of a recording device.

3. The method according to claim 1, wherein the applying step is performed by puncturing the patient's skin with a needle having a substance applied thereon.

4. The method according to claim 1, wherein the applying step is performed by application of a substance on the skin.

5. The method according to claim 1, wherein in the measuring step a greatest dimension $S_T$ of the allergen-induced hyperthermia in the third region, a greatest dimension $S_H$ of the histamine-induced hyperthermia in the first region and a greatest dimension $S_N$ of the sodium chloride-induced hyperthermia in the second region are associated with their relevant color changes of a thermochromic layer of the planar thermosensitive detector.

6. The method according to claim 5, wherein in the comparing step the hyperthermic allergic reaction is deemed positive (the test substance is an allergen) if a result of following operation $$\frac{S_T - S_N}{S_H - S_N}$$

is greater than or equal to 1.

* * * * *